(12) United States Patent
Hamlin

(10) Patent No.: US 6,168,433 B1
(45) Date of Patent: Jan. 2, 2001

(54) DIRECT DRIVE DENTAL PROPHY ANGLE

(76) Inventor: David A. Hamlin, 15 Parkside Dr., Langhorne, PA (US) 19047

(*) Notice: Under 35 U.S.C. 154(b), the term of this patent shall be extended for 0 days.

(21) Appl. No.: 09/451,988

(22) Filed: Nov. 30, 1999

(51) Int. Cl.$^7$ ............................................ A61C 3/06
(52) U.S. Cl. .................................................. 433/125
(58) Field of Search ............................ 433/125, 112, 433/114

(56) References Cited

U.S. PATENT DOCUMENTS

| | | | |
|---|---|---|---|
| 118,237 | 8/1871 | Hartman | 433/114 |
| 1,534,657 | 4/1925 | Patterson | 433/114 |
| 1,927,566 | 9/1933 | Hawk | 433/125 |
| 2,135,933 | 11/1938 | Blair | 433/126 |
| 3,472,045 | 10/1969 | Nelson, et al. | 433/112 |
| 3,727,313 | 4/1973 | Graham | 433/125 |
| 3,740,853 | 6/1973 | Brahler | 433/125 |
| 3,757,419 | 9/1973 | Hopkins | 433/125 |
| 3,822,432 | 7/1974 | Skinner | 15/23 |
| 3,869,877 | 3/1975 | Brahler | 64/2 |
| 4,014,098 | 3/1977 | Scrivo et al. | 433/29 |
| 4,060,870 | 12/1977 | Cannarella | 15/24 |
| 4,075,761 | 2/1978 | Behne et al. | 32/27 |
| 4,182,041 | 1/1980 | Girard | 433/115 |
| 4,490,113 | 12/1984 | Kawada | 433/104 |
| 5,020,994 | 6/1991 | Huang | 433/126 |
| 5,028,233 | 7/1991 | Witherby | 433/125 |
| 5,040,978 | 8/1991 | Falcon et al. | 433/125 |
| 5,145,370 | 9/1992 | Woodward | 433/126 |
| 5,169,312 | 12/1992 | Berlin | 433/123 |
| 5,209,658 | 5/1993 | Brahler | 433/125 |
| 5,352,119 | 10/1994 | Sakurai | 433/125 |
| 5,356,340 | 10/1994 | Miller et al. | 464/87 |
| 5,374,189 | 12/1994 | Mendoza | 433/125 |
| 5,423,679 | 6/1995 | Bailey | 433/125 |
| 5,433,605 | 7/1995 | Strobl, Jr. | 433/112 |
| 5,496,218 | 3/1996 | Brahler | 464/182 |
| 5,503,555 | 4/1996 | Bailey | 433/126 |
| 5,529,495 | 6/1996 | Edwards | 433/112 |
| 5,531,599 | 7/1996 | Bailey | 433/125 |
| 5,645,426 | 7/1997 | Grim et al. | 433/125 |
| 5,730,595 | 3/1998 | Bailey | 433/125 |

FOREIGN PATENT DOCUMENTS 743770  6/1944  (DE).

OTHER PUBLICATIONS

"Comparison of Two Prophylaxis Angles: Disposable and Autoclavable", Dean et al., JADA, vol. 128, pp. 444–446.

*Primary Examiner*—John J. Wilson
(74) *Attorney, Agent, or Firm*—Henry H. Skillman; Dann, Dorfman, Herrell & Skillman

(57) ABSTRACT

A dental prophy angle adapted to be engaged with a dental handpiece having a nose cone and a low-speed rotary driver within the nose cone. The prophy angle has a proximal end adapted to releasably engage with said nose cone, and a distal end having an implement-mounting member rotatable therein. A flexible shaft extends from the nose cone through the angle to the mounting member and has a diameter which is substantially smaller than the interior wall of the prophy angle. The shaft has a coupling member with a free axial end adapted to engage the rotary driver in the nose cone to be rotated upon rotation of said driver, and an opposite captive end connected to said shaft with a shoulder surrounding said flexible shaft and facing away from said free end to confront an abutment limiting axial displacement of said coupling member within the prophy angle. The flexible shaft is a steel cable comprising a plurality of multi-stranded steel cords twisted together to form a cable and encased in a sheath of polytetrafluoroethylene.

11 Claims, 1 Drawing Sheet

DIRECT DRIVE DENTAL PROPHY ANGLE

FIELD OF THE INVENTION

The present invention relates to dental equipment, and more particularly to an attachment for a dental handpiece for mounting in a dental cleaning implement for use in prophylaxis procedures.

BACKGROUND OF THE INVENTION

Dental prophy angles are used in the final step of the dental cleaning visit that practically all patients receive annually. There are marketed various disposable prophy angles, dental prophylaxis angles, that are believed represented by the disclosures of U.S. Pat. Nos. 5,040,978, 5,645,426, 5,352,119, 5,730,595 and 5,156,547. It is recognized that the making of inexpensive prophy angles enables the dental professional or hygienist to discard the prophy angle rather than have to sterilize the unit for re-use. It is further recognized that making a disposable prophy angle (DPA) which is reliable enough to perform complete prophy on a single patient without failure eliminates the time cost and inconvenience associated with refitting the handpiece with a subsequent unit or units during the prophylaxis procedure.

Conventional DPA's are true analogs of the standard Doriot style prophy angle, using the same type of gear geometry. The advantage of this known system is to allow for a "use once and dispose" of a previously high labor cost item (clean, sterilize, and lube between patients). In the past, a number of the units would fail because of poor fit of the gears and their support housing. While a number of companies have engineered better tolerances and materials to overcome these problems, failure of the units still remains as a factor in the field.

An additional factor is patient discomfort which results from various degrees of vibration, noise, and heat generated by existing DPA's while in use. Patient comfort remains a fundamental need for products in this category and improvements are always welcome.

An additional factor in the prophylaxis procedure is that the dentition requires the hygienist or dentist to change their handpiece orientation to clean all surfaces. The majority of the presently marketed prophy angles are rigidly fixed at a 90° angle and therefore do not allow adaptability of the DPA to accomplish conformation to various angles of the dentition without manipulating the entire handpiece with the attached DPA. This may become even more important as additional controls are incorporated onto the handpiece itself.

SUMMARY OF THE INVENTION

A failure-free disposable prophy angle of comparable or lower cost to presently available gear-driven angles for use in the dental field. Alternate embodiments include angle and/or rotational flexibility to the user without changing the handpiece orientation in the user's hand.

The invention provides a dental prophy angle design wherein the rotary force, supplied by a standard low speed dental handset, is transferred directly to the prophy cup eliminating gear transmission. The angle between the axis of rotation of the prophy cup and axis of rotation of said externally supplied force is preferably at a given divergent angle, normally approximately 90°. Alternative embodiments of the invention allow for a variety of angles and rotational orientations between the axis of rotation of the prophy cup and the drive axis of said externally supplied force in a prophy angle housing as required by the user. The entire unit has suitable durability to assuredly perform without failure for the period required to perform the polishing of an entire dentition of a single dental patient.

BRIEF DESCRIPTION OF THE DRAWING

All of the objects of the present invention are more fully set forth hereinafter with reference to the accompanying drawings, wherein.

DETAILED DESCRIPTION OF THE PREFERRED EMBODIMENTS

Figure 1:
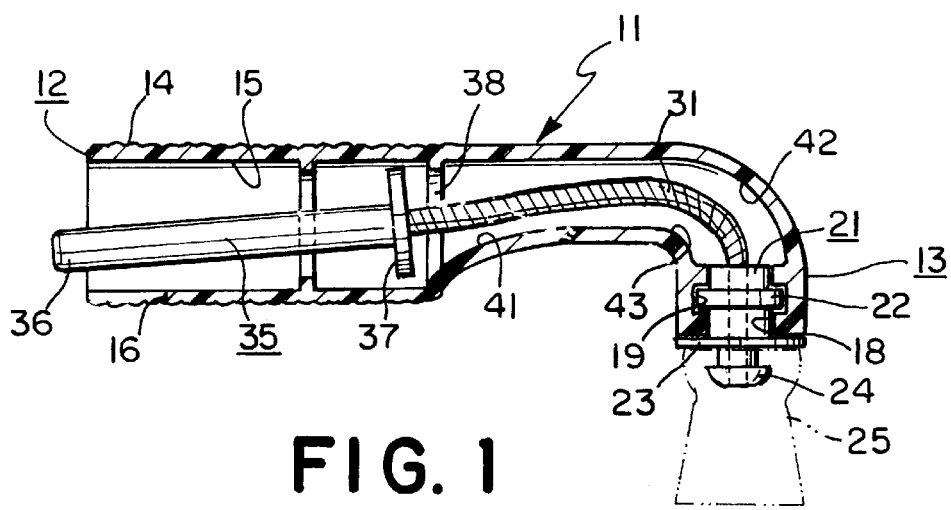
FIG. 1 is a longitudinal cross-section illustrating a prophy angle made in accordance with the present invention.

FIG. 1 shows a preferred embodiment of the prophy angle in accordance with the present invention. The prophy angle 11 shown in FIG. 1 has a generally tubular housing having a proximal end 12 and a distal end 13. At the proximal end, there is a hollow tubular wall 14 defining within the wall a hollow tubular drive chamber 15. Preferably, the wall 14 is cylindrical in form to engage and support the prophy angle in the nose cone of a dental handpiece. The outside peripheral surface of the wall 14 has shallow ribs to frictionally engage within the nose cone of the handpiece. The nose cone has a projecting lug which engages in a recess 16 to anchor the prophy angle 11 against inadvertent rotation in the handpiece. The lug may be replaced by other forms of anti-rotation stops.

The distal end 13 of the prophy angle has an axial passage 18 with a peripheral internal groove 19. An implement-mounting member 21 is mounted in the passageway 18 and the member has a flange 22 which engages in the groove 19. The axial passage 18 provides a bearing surface affording rotation of the member 21, the groove 19 capturing the flange 22 so as to prevent inadvertent axial displacement of the member 21. The member 21 is preferably formed of a non-friction material so as to freely rotate within the passage 18. At the open end of the passage 18, the member 21 is provided with a deflector 23 which serves to limit the infiltration of particles and droplets generated during the use of the cleaning implement. Beyond the deflector 23, a button 24 is provided to releasably mount the prophy cleaning tool shown in broken lines at 25. In the present embodiment of the invention, the distal end of the prophy angle is disposed at a right angle to the axis of the nose cone and the drive chamber 15. In the present embodiment, the right angular projection of the distal end is positioned to diverge from the extended axis of the chamber 15 in the same downward direction as the circumferential position of the recess 16 about the axis.

In accordance with the invention, the mounting member 21 is coupled to the rotary driver within the nose cone of the handpiece by a flexible shaft 31 extending from the member 21 at the distal end of the prophy angle through the hollow tubular housing and terminating in the chamber 15. The housing of the prophy angle 11 provides a continuous channel from the distal end to the proximal end and, as shown in FIG. 1, the channel 41 has a narrow mid-portion which flares outwardly towards the chamber 15 at the proximal end and towards the passageway 18 at the distal end 13. The minimum width of the channel 41 is at least twice the thickness of the flexible shaft 31 so as to allow the shaft to accommodate flexure by lateral displacement toward and away from the internal walls of the channel.

At the proximal end, the flexible shaft 31 has a connector 35 which is operable to be engaged within the rotary driver which is located centrally within the nose cone of the handpiece. As shown, the connector 35 comprises a free end with a cylindrical stub 36 which is adapted to be frictionally engaged in the rotary driver of the nose cone. At the other end, the connector 35 has a flange 37 which fits loosely within the interior wall 14 of the chamber 15. At the inner end of the chamber 15, the interior wall 14 terminates in an abutment 38 which serves as a barrier between the chamber 15 and the channel 41. The abutment 38 provides a continuation of the passage 41 into the chamber 15, but the internal perimeter of the abutment 38 is smaller than the outer perimeter of the flange 37 so that the abutment 38 serves to provide a support for positioning the stub 36 concentrically within the chamber 15 during initial engagement of the stub 36 with the rotary driver of the nose cone. When the flange 37 engages the abutment 38, the flexible shaft 31 is flexed towards the wall of the channel at 42 where the channel is curved to accommodate the angular position of the passage 18 in the distal end of the prophy angle relative to the axis of the chamber 15. When the shaft 31 is flexed towards the outside wall 42 of the curve, it also is flexed away from the inside wall 43 of the curve.

In order to have a prolonged effective life of the flexible shaft 31, it is desirable to support the shaft 31 at a single location within the prophy angle during use and rotation of the flexible shaft. To this end, the mounting member 21 provides the sole support for the flexible shaft at the distal end, the shaft being supported by the connector 35 at the proximal end within the rotary driver of the nose cone. When supported at these points, the flange 37 is separated from the abutment 38 and the mounting member 21 is freely rotatable in the passageway 18. Preferably, the material of the member 21 is of anti-friction material, but it is also contemplated that if the member 21 is subject to friction, the passageway 18 and groove 19 may be lined with anti-friction material.

Prior attempts to employ a flexible shaft in a prophy angle have led to premature failure of the shaft. In accordance with the present invention, the flexible shaft of the present invention comprises a stainless steel cable sheathed in polytetrafluoroethylene (Teflon), for example supplied by McMaster-Carr Part No. 3423T29, which is a 1/16" stainless steel wire rope having nine cords twisted together, each cord comprising 19 strands of stainless steel wire. The 1/16" diameter of the sheathed wire rope fits loosely within the 3/16" width of the channel 41 at its narrowest point. Since the rope occupies one-third of the width of the channel, there is little tendency for the rope to engage the walls of the channel and generate friction which would cause deterioration of the cable drive. A wire rope of this character is effective to rotationally drive the member 21 with a minimum generation of friction and heat.

A sheathed cable of this type withstands a severe radius of curvature while under the rotational forces generated by rotation of a standard low-speed dental handpiece in the range of 0–50,000 rpm and under loads equal to those found while polishing the dentition utilizing a standard dental prophy cup. The wire will perform without fracture, splitting, seizing or other forms of failure that would interfere with the rotation of the mounting member 21. Other cables of similar nature which may vary in materials composed thereof of geometries employed in the assemblage, or relative sizes utilized may be found to achieve the same or similar end results.

In order to accommodate the desire to use prophy angles with angles other than 90°, as shown in FIG. 1, several prophy angles may be supplied in which the housings 11 are formed to provide different angles as requested by the dental technician, hygienist or dentist.

Figure 2:
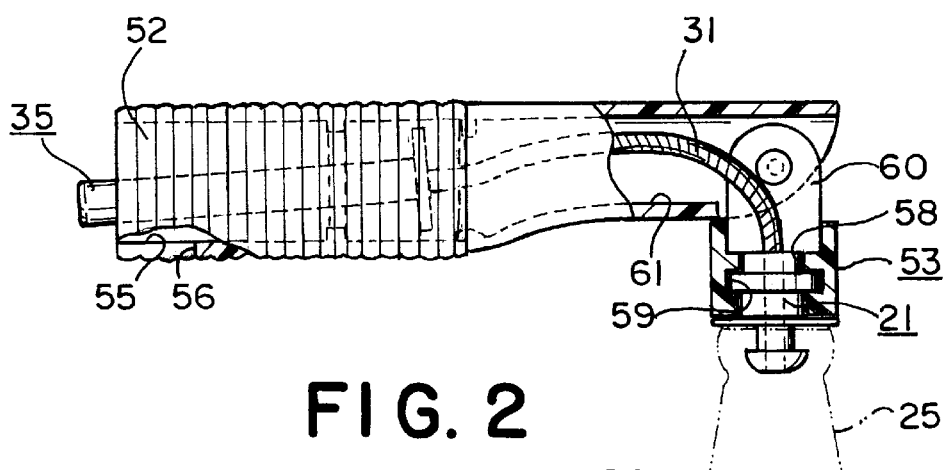
FIG. 2 is a side elevation of a second embodiment of the prophy angle with portions broken away illustrating angular adjustability of the distal end part.

Instead of providing a plurality of prophy angles in which the projection of the distal end from the chamber axis is fixed, the prophy angle may be made in two parts, as shown in FIG. 2. In this embodiment of the invention, a prophy angle 51 has a proximal end part 52 and a distal end part 53. The proximal end part has a drive chamber 55 with a recess 56 for engagement with the nose cone of the handpiece. At the remote end of the proximal part 52, a yoke 60 mounts the distal end part 53 for angular adjustment. Like the distal end 23 of the embodiment shown in FIG. 1, the distal end part 53 has an axial passage 58 with an annular recess 59 to provide a bearing for a mounting member 21 of a flexible drive assembly which may be identical to the assembly shown in FIG. 1. The member 21 serves as the sole rotary support for the flexible drive shaft 31 which extends rearwardly through the channel 61 in the housing of the prophy angle 51. The flexible shaft 31 has a connector 35 with a stub 36 for engagement with the rotary drive of the nose cone, similarly to the engagement provided in the embodiment of FIG. 1. As shown, the angle of the axis of the passage 58 diverges from the extended axis of the chamber 55 at an adjustable angle which, in FIG. 2, is 90°. The yoke is frictionally engaged with the remote end of the proximal end part 52 with a friction coupling to enable adjustment of the yoke 60 to varying angles between 0–90°. As in the embodiment of FIG. 1, the flexible cable 31 preferably comprises a multi-stranded stainless steel cable having a teflon coating.

Figure 3:
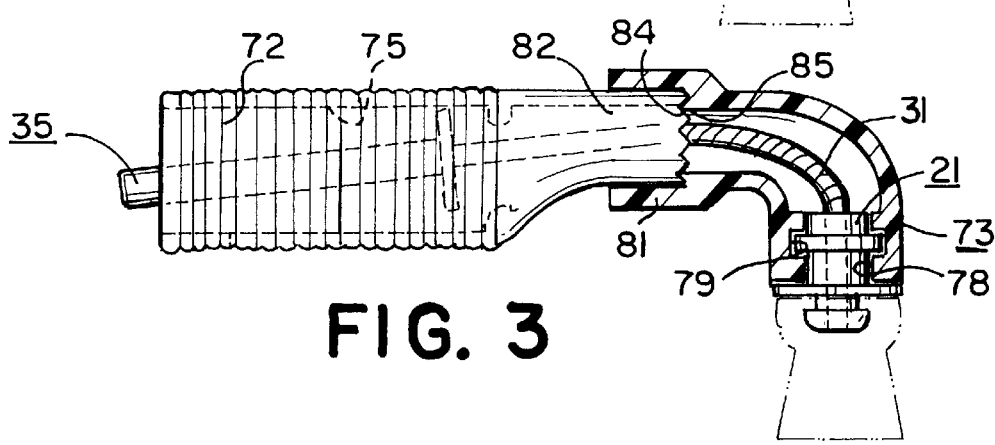
FIG. 3 is a side elevation, partially in section, of a third embodiment of the prophy angle made in accordance with the present invention with the distal part of the angle shown in section to illustrate the circumferential adjustability thereof.

The embodiment of FIG. 2 provides for adjustment of the angle of the passage axis relative to the axis of the chamber 55, with the passage axis diverging from the chamber axis at a position corresponding to the position of the recess 56 circumferentially in the chamber 55. Where it is desired to adjust the position of divergence circumferentially of the chamber 55, an alternate embodiment may be provided, as shown in FIG. 3. In this embodiment of the invention, the prophy angle is made with a proximal part 72 and a distal part 73. The embodiment of FIG. 3 is designed to cooperate with a flexible drive assembly identical to the drive assembly shown in FIGS. 1 and 2. To this end, the distal part 73 has an axial passageway 78 with a recess 79 to serve as a bearing for the mounting member 21 of the flexible shaft assembly shown in the previous figures. The assembly includes the member 21, the flexible shaft 31 and the connector 35. In the present instance, the near end of the distal part 73 has an enlarged cylindrical socket 81 which telescopically engages a hollow cylindrical plug portion 82 at the remote end of the proximal part 72. The free end of the plug part 82 has axially-projecting teeth 84 which cooperate with corresponding teeth 85 in the socket part 81. The socket part 81 is frictionally engaged with the plug part 82 and when fully engaged, the teeth 84 mesh with the teeth 85 to anchor the socket part against rotation about the common axis of the plug and socket. When it is desired to adjust the circumferential position of the divergence of the passage axis, the plug and socket are separated sufficiently to disengage the teeth and enable rotation of the socket 81 on the plug 82 to reposition the passage at a different position relative to the circumference of the chamber 75. The prophy angle of FIG. 3 may be provided with different angles of divergence between 0° and 90°, according to the desires of the dental technician, hygienist or dentist and may also be provided with an adjustable yoke as described in connection with the embodiment shown in FIG. 2.

While particular embodiments of the invention has been herein illustrated and described, it is not intended to limit the invention to such disclosures, but changes and modifications may be made therein and thereto within the scope of the following claims.

I claim:

1. A dental prophy angle adapted to be engaged with a dental handpiece having a nose cone and a low-speed rotary driver within the nose cone, said prophy angle comprising a tubular housing having a proximal end and a distal end, said proximal end comprising a hollow tubular wall adapted to releasably engage with said nose cone, and defining an axial drive chamber surrounding the rotary driver in said nose cone, said distal end having an axial central passage with a peripheral internal groove providing an annular bearing surface, said tubular housing wall providing a channel having an open width extending continuously from said chamber to said internal groove, the axis of said passage diverging at a given angle from the axis of said chamber, an implement-mounting member rotatable in said central passage, said member having an outside mount positioned outboard of said passage and an inside flange captured in said groove, said flange having an exposed surface confronting the annular bearing surface of said groove, at least one of said surfaces comprising an anti-friction material, said rotatable member operable to mount a dental cleaning device on said outside mount for rotation with said member, a flexible shaft having a connection to said rotatable member at one end and extending from said connection through said channel and having a terminal within said chamber, said flexible shaft having a diameter which is substantially smaller than the open width of said channel so as to be free to be spaced away from the tubular housing wall, and a coupling member having a captive axial end mounted on said shaft terminal in said chamber, said coupling member having a free axial end adapted to engage the rotary driver in the nose cone to effect rotation of said flexible shaft upon rotation of said driver, said captive end being connected to said shaft terminal within said chamber, said coupling member being spaced from said hollow tubular wall of said chamber throughout the length of said member from said free end to said captive end, and said shaft being spaced from said hollow tubular wall from said captive end of the coupling member into said channel.

2. A prophy angle according to claim 1, said coupling member having a shoulder surrounding said flexible shaft and facing away from said free end, said hollow wall of the chamber having an abutment confronting said shoulder and limiting axial displacement of coupling member during engagement of the coupling member with the rotary driver.

3. A prophy angle according to claim 2, wherein said tubular housing has a curve between said distal and proximal ends, said housing curve having an inside wall and an outside wall, said abutment engaging said shoulder to limit axial displacement of said shaft terminal whereby said flexible shaft does not touch said outside wall, said shaft being out of contact with said inside and outside walls when said connection is engaged with said rotary driver.

4. A prophy angle according to claim 1 wherein said channel has a width at least twice the diameter of said flexible shaft between said central passage and said chamber.

5. A prophy angle according to claim 1 wherein said proximal and distal ends of said tubular housing are separate parts, and including means mounting said separate parts for relative adjustment, said distal end part being adjustable to vary said given angle of divergence between the axes of said chamber and said passage.

6. A prophy angle to claim 5 including swivel connecting said distal end part to said proximal end part, said swivel having a pivotal axis perpendicular to both the chamber axis and the passage axis.

7. A prophy angle according to claim 1, said chamber including a stop to determine the circumferential position of said prophy angle on said nose cone and thereby the direction at which said passage axis diverges from said chamber axis, said proximal and distal ends of said tubular housing being separate parts, and including means mounting said separate parts for relative adjustment, said distal end part being adjustable circumferentially about the axis of said chamber to vary the direction at which said given angle causes said passage axis to diverge from the axis of said chamber.

8. A prophy angle according to claim 7, wherein said proximal end part has a cylindrical plug portion coaxial with said chamber axis, and said distal end part has a cylindrical socket portion coaxial with said chamber axis, said plug and socket portions being telescopically engaged and having teeth which are selectively engageable to determine the relative circumferential positions of said plug and socket.

9. A prophy angle according to claim 7 for use with a nose cone having a projecting lug for engaging the prophy angle, said chamber having a recess adapted to engage the lug of said nose cone and serve as said stop for determining the circumferential position of the prophy angle.

10. A dental prophy angle adapted to be engaged with a dental handpiece having a nose cone and a low-speed rotary driver within the nose cone, said prophy angle comprising a tubular housing having a proximal end and a distal end, said proximal end comprising a hollow tubular wall adapted to releasably engage with said nose cone, and defining a axial drive chamber surrounding the rotary driver of said nose cone, said distal end having an axial central passage and an implement-mounting member rotatable in said central passage, said tubular housing providing a channel extending continuously from said chamber to said passage, said channel having a minimum internal diameter of approximately 0.375", said member operable to mount a dental cleaning device outboard of said distal end, a flexible shaft having a connection to said member at one end and extending from said connection through said channel and having a terminal within said chamber, said flexible shaft having a diameter of approximately 0.125" which is substantially smaller than the width of said channel so as to be free for lateral displacement away from the hollow interior wall of said housing, and a coupling member mounted on said shaft terminal in said chamber to engage said rotor driver, said flexible shaft being a steel cable comprising a plurality of multi-stranded steel cords twisted together to form a cable, said twisted cords being encased in a sheath of plastic resinous nonstick material.

11. A prophy angle according to claim 10, wherein said shaft comprises seven cords, and each cord comprises 19 strands of steel wire, said sheath being comprised of polytetrafluoroethylene.

* * * * *